(12) United States Patent
Fleury et al.

(10) Patent No.: US 6,185,985 B1
(45) Date of Patent: Feb. 13, 2001

(54) PROCESS AND DEVICE FOR MEASURING PHYSICAL CHARACTERISTICS OF A POROUS SAMPLE BY CENTRIFUGAL DISPLACEMENT OF FLUIDS

(75) Inventors: Marc Fleury, La Celle Saint Cloud; Philippe Poulain, Carrières s/Poissy; Jean-Claude Marchand, Paris; Gabriel Ringot, Courbevoie, all of (FR)

(73) Assignee: Institut Francais du Petrole, Rueil-Malmaison Cedex (FR)

( * ) Notice: Under 35 U.S.C. 154(b), the term of this patent shall be extended for 0 days.

(21) Appl. No.: 09/206,983

(22) Filed: Dec. 8, 1998

(30) Foreign Application Priority Data

Dec. 11, 1997 (FR) .................................................. 97 15833

(51) Int. Cl.$^7$ .................................................. G01N 15/08
(52) U.S. Cl. .................................................. 73/38
(58) Field of Search ...................... 73/38, 304 C, 73/535; 702/52; 340/870.37; 494/22, 77; 34/60, 135, 341, 350

(56) References Cited

U.S. PATENT DOCUMENTS

| | | | |
|---|---|---|---|
| 3,344,982 | * 10/1967 | Todd | 494/22 |
| 3,644,821 | * 2/1972 | Long | 73/304 C |
| 3,683,674 | * 8/1972 | Roy | 73/38 |
| 3,974,695 | * 8/1976 | Lerner | 73/304 C |
| 4,122,718 | 10/1978 | Gustafson | 73/304 |
| 4,679,422 | * 7/1987 | Rubin et al. | 73/38 |
| 4,740,077 | 4/1988 | Goodwill | 356/23 |
| 5,069,065 | * 12/1991 | Sprunt et al. | 73/38 |
| 5,731,511 | * 3/1998 | Roque et al. | 73/38 |
| 6,011,490 | * 1/2000 | Tonnesen et al. | 494/10 |

FOREIGN PATENT DOCUMENTS

| | | |
|---|---|---|
| 653129 | 12/1985 | (CH) . |
| 0206372 | 12/1986 | (EP) . |
| 0473500 | 3/1992 | (EP) . |
| 0586001 | 3/1994 | (EP) . |
| 0603040 | 6/1994 | (EP) . |
| 971242 | 9/1964 | (GB) . |

* cited by examiner

Primary Examiner—Hezron Williams
Assistant Examiner—Michael Cygan
(74) Attorney, Agent, or Firm—Antonelli, Terry, Stout & Kraus, LLP (57) ABSTRACT

The invention is a process and device for performing successive drainage and imbibition phases of a first electrically-conducting fluid and a second fluid of lower density than the first fluid, in a porous sample (1) by means of a centrifuge. Each sample is placed in a main chamber (3) of an elongate vessel (2) fastened to the end of an arm of the centrifuge, together with a spacer (6) whose volume is so selected that, on the one hand, the interface between the two fluids does not come into contact with the sample in operation and, on the other hand, the volume of chamber (3) remaining free around the sample and the associated spacer is greater than, but preferably close to the pore volume of the sample, so as to maximize the displacement amplitude of the interface for a given variation of the volume of fluid displaced. A capacitive sonde (11) in an auxiliary cavity (4), connected to an outer measuring device, is used for measuring the displacements of the interface. The invention has applications of surveying of rocks taken from an underground reservoir.

19 Claims, 4 Drawing Sheets

PROCESS AND DEVICE FOR MEASURING PHYSICAL CHARACTERISTICS OF A POROUS SAMPLE BY CENTRIFUGAL DISPLACEMENT OF FLUIDS

BACKGROUND OF THE INVENTION

1. Field of the Invention

The present invention relates to a process and to a device for measuring physical characteristics of a porous sample by centrifugal displacement of fluids.

2. Description of the Prior Art

It is important to determine the wettability of rocks with regard to the water and to the oil which may be contained therein. The rock must therefore be subjected to a drainage process, i.e. displacement of the fluids intended to decrease the water saturation, followed by an imbibition process, this term being to a displacement of the fluids which increases the water saturation (Sw) of the rock. The capillary pressure at one point is defined as the difference Pc at equilibrium between the pressure Po of the oil and the pressure Pw of the water. This parameter makes sense only if the two fluids are in the continuous phase in the porous medium. For a water wet medium, only positive values make sense. On the other hand, if the medium has a mixed wettability, the fluids can remain in the continuous phase for the positive and for the negative capillary pressures (Pc) as well.

Figure 1:
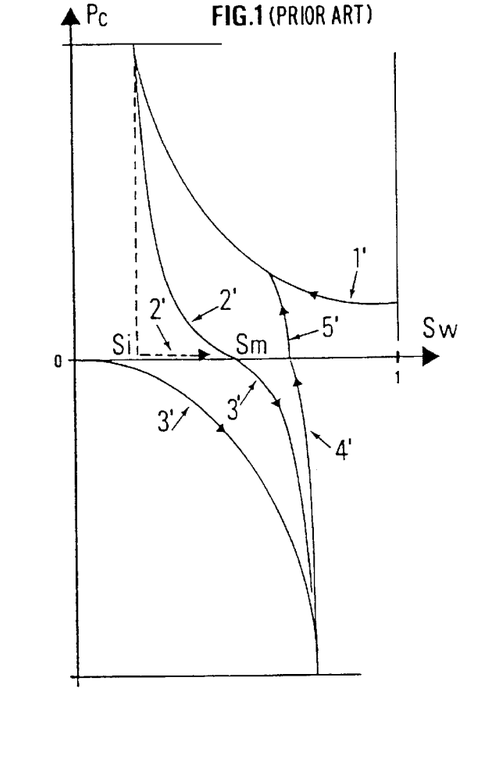
FIG. 1 shows various curves representative of the saturation variations of a sample during a drainage-imbibition cycle.

For an application of this type, a prior art complete capillary pressure measuring cycle must therefore comprise (FIG. 1):

a) positive primary drainage of an initially 100% water-saturated sample (curve 11),
b) positive imbibition (curve 2'),
c) negative imbibition (curve 3'),
d) negative drainage (curve 4'), and
e) positive secondary drainage (curve 5').

Knowledge of various parameters and notably of the wettability of rocks is useful notably when enhanced recovery is to be performed in a formation, by draining the effluents contained therein by injecting a fluid under pressure, and when the most suitable fluid (water or gas) for effluents displacement is to be determined by means of preliminary tests.

The invention also finds applications in civil engineering for field hydrology purposes in order to evaluate the degree of pollution for example, or in the building industry to test construction materials, notably in order to select waterproofing treatments for example.

French Patent 2,763,690 filed by the assignee describes a method allowing measurement of physical characteristics of saturated rocks by subjecting them to a progressive-speed centrifugation and by measuring the amount of fluid displaced as a function of the rotating speed. The sample saturated with a liquid A for example is placed in an elongate container or vessel containing another fluid B of different density. The vessel is fastened to the end of a rotating arm and a centrifugal force is applied thereto so as to study fluid displacements in the sample during at least two distinct phases. During a first drainage phase, the assembly is then subjected to a centrifugal force applied along the length of the vessel so as to exert an expulsion force thereon, which tends to cause part of first fluid B to flow out. At the same time, some of fluid A flows into the sample. The two fluids move inside the sample until a position of equilibrium is reached, where the force due to the capillary pressure in the pores compensates for the centrifugal force exerted.

It is well-known that the capillary pressure $P_C$ at a distance R from the fulcrum pin, when it is positive, is expressed by the following relation:

$$P_C(R) = \tfrac{1}{2}\Delta\rho\omega^2(R^2_{max} - R^2) \ P_C(R_{max}) = 0$$

where $\omega$ is the angular rotating speed, $R_{max}$ is the distance from the base of the sample bar S to the fulcrum pin, $\Delta\rho$ is the difference between the respective densities of the two fluids.

For negative values, the capillary pressure $P_C$ at a distance R from the fulcrum pin is:

$$P_C(R) = \tfrac{1}{2}\Delta\rho\omega^2(R^2{min} - R^2) \ P_C(R_{min}) = 0.$$

During the re-imbibition phase (curve 2'), the speed is decreased in order to study the re-integration of the initial fluid therein. With this type of method, local saturations are calculated by means of an inversion program from the total amount of water expelled from the sample.

The capillary pressure in the sample can be deduced from the precise measurement of the amount of initial fluid extracted as a function of the centrifugal force exerted and from the variation of the average fluid saturation $S_m$ of the sample as a function of the centrifugal force exerted, which is obtained by acoustic detection for example.

With a fluid-saturated sample, it can be seen (FIG. 1) that the saturation during the centrifugal drainage phase, for a determined radius r, decreases (curve 1') as the rotating speed w increases until a minimum value Si is reached. During this drainage phase, the rotating speed is increased in successive stages until a speed of 3500 rpm is reached for example. The fluid saturation variations are measured during the deceleration phase. A hysteresis phenomenon and a return, according to another variation curve (curve 2'), to a relative maximum value Sm are observed during the phase of re-imbibition of the porous material.

A system allowing maintenance of the drained fluid in contact with the sample bar is preferably used so that, when the deceleration phase starts, the bar can be properly re-imbibed. To ensure this maintenance, the system stabilizes the interface level between the two fluids at a minimum level where it is level with the base of the bar, i.e. at the furthest distance from the fulcrum pin ($R_{max}$), at least throughout the deceleration phase. Such a system is easy to implement but it requires a pump borne by the arm and capable of withstanding the high accelerations required for implementation of the system, typically about 3000 g.

Patent application EN.97/06,434 filed by the assignee also describes a centrifugal type device allowing to measure physical characteristics of a porous solid sample by means of successive drainage and imbibition phases, in the presence of a first electricity-conducting fluid (such as brine for example) and of a second fluid of lower density than the first fluid (such as oil for example). It includes a rotatably mobile equipment comprising an elongate container or vessel (preferably at least a pair of vessels) provided with an inner cavity for the sample, each vessel being mounted swivelling at the end of an arm driven in rotation so as to apply a centrifugal force thereon in the direction of elongation of the vessel. A hydraulic system allows forcing displacement of the fluids and a capacitive sonde placed in the vessel, in the direction of elongation thereof, is used in order to continuously follow the displacements of the interface between the two fluids in the vessel. It is externally connected to a measuring device by an electro-hydraulic rotating connector.

This device can detect variations of the brine level with very high accuracy but its implementation requires a relatively costly rotating electro-hydraulic connector if perfect sealing is to be maintained.

SUMMARY OF THE INVENTION

The device according to the invention allows measurement of physical characteristics of at least one porous solid sample by performing successive drainage and imbibition phases, in the presence of a first electrically-conductive fluid and of a second fluid of lower density than the first fluid. It comprises a centrifugation assembly including at least one elongate vessel provided with a first chamber for the sample, each vessel being fastened to the end of an arm secured to a hub, a motive drive which drives the arm in rotation and creates a centrifugal force exerted in the direction of elongation of the vessel, and a measuring and control system comprising a detector which detects the position, in each vessel, of the interface between the first and the second fluid.

A tool in accordance with the invention is notably well suited to test geologic samples and to determine various parameters such as the capillary pressure of rocks in drainage and imbibition phases, their wettability index, their relative permeability, their resistivity index, etc.

The device finds applications notably in the petroleum domain for testing rocks which have been taken from reservoirs containing or likely to contain petroleum effluents.

The device comprises, in each first chamber, a spacer situated after the sample, the volume of the spacer being so selected that, in operation, the interface between the two fluids does not come into contact with the sample, the respective positions of the sample and of the associated spacer in the first chamber being inverted according to whether a drainage phase or an imbibition phase is carried out.

The volume of each spacer is preferably so selected that the free volume remaining in the first chamber around the sample and the spacer is at least equal to the pore volume of the sample and preferably close thereto, so as to maximize the position variation of the interface as a function of the fluid volume variation in the first chamber.

An embodiment of the device can include a container for the spacer made from an insulating material, with a cross-section larger than the cross-section of the spacer for collecting the fluid expelled from the sample, this vessel communicating with the detector which detects the position of the interface. The size of the container is preferably selected so that the total oil volume expelled from the sample substantially fills up the free volume in the container around the spacer thereby the range of displacement of the interface resulting from the variation of volume of the fluids in the first chamber can be optimized.

The detection, in each vessel, which detects the position of the interface between the two fluids preferably comprise a capacitive sonde placed in an auxiliary chamber communicating with the first chamber, connected by a rotating electric connector to a measuring device in the measuring and control system. This system comprises for example a micro-computer associated with a signal acquisition device of each sonde and with a control which controls the device, and it is suited to determine various physical parameters of the sample by taking account of the amounts to of fluid displaced in operation.

Each vessel comprises for example two channels communicating the opposite ends of the first chamber with the outside on the side of the end of the vessel which is the closest to the hub in operation, and caps for insulating the inside of the chamber during centrifugation.

The centrifugation assembly preferably comprises a pair of arms (or two pairs) and vessels placed in opposition at the end of each pair of arms in order to place samples therein.

The process for implementing the device according to the invention comprises drainage operations for draining a fluid out of each sample, including:

a) installation of each sample previously saturated with conducting fluid and of the associated spacer in the first chamber of a vessel, this spacer being placed at a further distance from the hub of the centrifugation assembly than the sample, b) injection of conducting fluid in a known amount into the first chamber on the side thereof occupied by the spacer, c) increasing the centrifugation speed in successive stages until a capillary equilibrium is reached for each stage, and d) acquisition of the signals coming from the sonde, representative of the position variation of the interface between the two fluids, and determination of the volumes of fluid displaced by the measuring and control system.

The conducting fluid is preferably removed from each vessel by injecting a volume of the other fluid, and the volume extracted is measured in order to corroborate the volume determined by the measuring and control system.

The samples can thereafter be subjected to forced imbibition operations comprising:

a) installing each sample and the associated spacer in the chamber of a vessel containing a conducting fluid, so that the spacer is closer to the hub than the sample, b) injecting, in each vessel, a known amount of the other fluid, c) increasing the centrifugation speed in successive stages until a capillary equilibrium is reached for each stage, and d) acquiring the signals from the sonde, representative of the position variations of the interface between the two fluids, and determining the volumes of fluid displaced by means of the measuring and control system.

The second fluid is preferably removed from each vessel by injecting a volume of conducting fluid, and the volume extracted is measured and compared with the volume determined by the measuring and control system.

In another embodiment of the process suitable for an gas-oil drainage of a sample includes installing a sample saturated with an insulating liquid (such as oil) in a vessel filled with a non-conducting gas (air for example), installing the spacer in a container made of an insulating material positioned in the vessel to collect the insulating fluid expelled from the sample, the container communicating with the detector which detects the position of the interface, injecting a volume of a conducting liquid with a density larger than the density of the insulating liquid, and measuring displacement of the interface between the conducting liquid and the gas by the detector.

The device according to the invention allows sample drainage and imbibition operations to be performed more simply and the interface between the two fluids to be accurately detected. Each vessel is connected, in operation, to the measuring device only by means of a purely electrical rotating connector, which is therefore less expensive. The characteristics thereof are very stable notably with regard to the rotating speed. The accuracy obtained by using the capacitive sonde for measuring the interface level between the two liquids leads to an equal accuracy when measuring the saturation in the sample and allows determination of the capillary pressure in the part of the bar between the interface and the face that is the closest to the fulcrum pin.

BRIEF DESCRIPTION OF THE DRAWINGS

Other features and advantages of the device according to the invention will be clear from reading the description hereafter of embodiments given by way of non limitative example, with reference to the accompanying drawings wherein.

DETAILED DESCRIPTION OF THE INVENTION

I) Device

In order to subject porous rock samples 1 to a centrifugation operation, elongate containers or vessels 2 comprising each (FIGS. 2, 3) a first main chamber 3 and a second, tubular lateral chamber 4 communicating with the first chamber are used. Sample 1, previously associated with two plates 5A, 5B on the two end faces thereof, is placed in chamber 3. It occupies only part of the volume (half thereof for example). The other part comprises a solid cylindrical part or spacer 6. The cross-section thereof is so selected that the remaining volume of chamber 3 around it and sample 1 is at least equal to the volume of the pores of the sample.

Figure 6:
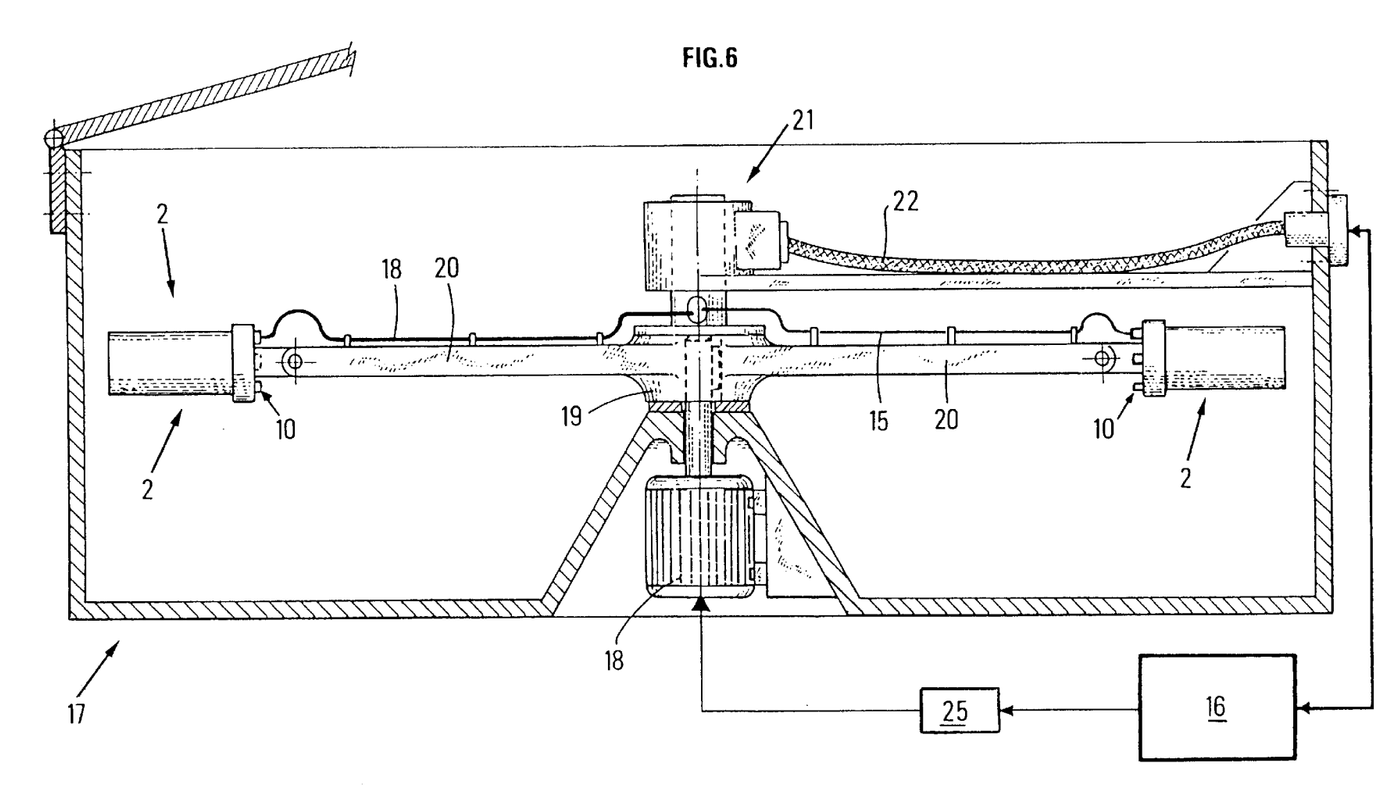

One of the ends 7 of the vessel comprises means (not shown) for securing it to a rotating driving assembly (centrifuge) such as that shown in FIG. 6. Two channels 8, 9 communicating respectively with the opposite ends of chamber 3 and closed by a screwed cap 10 open onto this end.

A capacitive type level-detecting sonde 11 is placed in tubular lateral chamber 4. It is suited to detect the interface variation, in lateral chamber 4, between an electrically conductive fluid such as brine and a non-conducting fluid such as oil. This sonde 11 comprises (FIG. 4) a first electrode 12 consisting of a metallic rod coated with a thin layer 13 of a dielectric material such as Teflon® or a glass ceramic for example, and a second bare metallic electrode 14 (a conducting wall of chamber 4 for example) whose potential is used as a reference datum.

Figure 4:
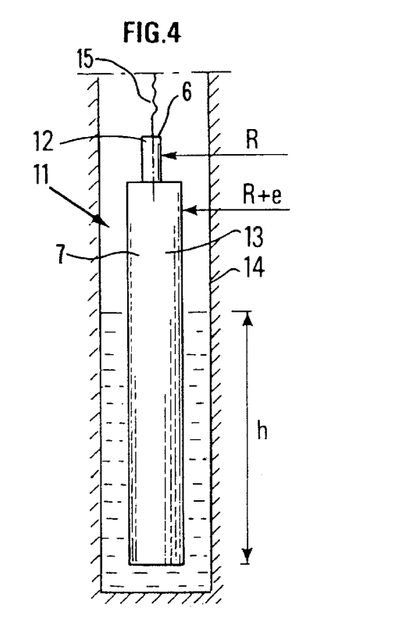
FIG. 4 illustrates the calculation of the capacity variation of the sonde as a function of the level variation of the conducting liquid expelled from the sample in operation.

The inter-electrode capacitance is expressed as follows:

$$c = 2\Pi\varepsilon_0\varepsilon_r\left[\ln\left(\frac{R+e}{R}\right)\right]^{-1} h \approx 2\Pi\varepsilon_0\varepsilon_r\frac{R}{e}h, \text{ where}$$

R is the radius of rod 6, e the thickness of the sheath or coating 7 surrounding the rod, $\in_r$ the relative dielectric constant of the material of the sheath, $\in_0$ the dielectric constant of the vacuum whose value is 8.859 $10^{-12}$ A.s/V.m, h the variable length of the sonde immersed in the conducting fluid.

Sonde 11 is connected to a conducting cable 15 linked to a measuring device 16 (FIG. 6) described hereafter.

Figure 5:
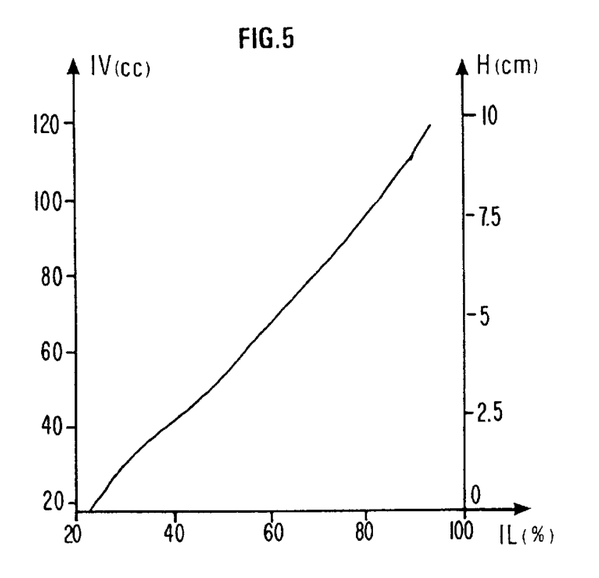
FIG. 5 shows an example of percentage variation (IL) of the signal delivered by the sonde of FIG. 4 as a function of the height H (and of the volume IV) of brine in the vessel, FIG. 6 diagrammatically shows the layout of a centrifugation assembly, the vessels driven in a horizontal position under the effect of the centrifugal force.

Any variation h in the conducting fluid level in the vessel is translated into a capacitance variation of the sonde. When using an electrode with a 3-mm radius and a 0.05-mm seal coating, a sonde capacitance variation ranging between 10 and 1000 pF is for example obtained. Prior to using it, the sonde is calibrated by indicating to the associated measuring device 16 the minimum level (0%) and the maximum level (100%) between which the brine level can range in the vessel during operation. The response curve of the sonde as shown in FIG. 5 is thus established.

In order to obtain the highest sensitivity possible, i.e. the greatest possible variation of the interface level for a given volume variation, the volume of spacer 6 is so adjusted that the free volume remaining around the spacer and the free volume around the sample are very close to each other.

The centrifuge comprises (FIG. 6) a tank 17, an electric motor 18 whose shaft drives a hub 19 into rotation. Two (or four) identical arms 20 are mounted in opposition two by two on hub 19. Containers or vessels 2 are mounted swivelling at the ends of each of the arms 20 as to spontaneously line up with the direction of the centrifugal force applied, and they balance each other in rotation. A sample 1 associated with a spacer 6 placed in each vessel 2.

Cables 15 associated with the various capacitive sondes 11 are connected to a multi-line rotating electric connector 21 of a well-known type borne by hub 19. The stator of this rotating connector 21 is connected by a cable 22 to the device 16. The rotating connector can comprise for example twelve channels allowing connection of four vessels 2 to device 16, in the configuration where the centrifuge comprises four arms 20.

Figure 7:
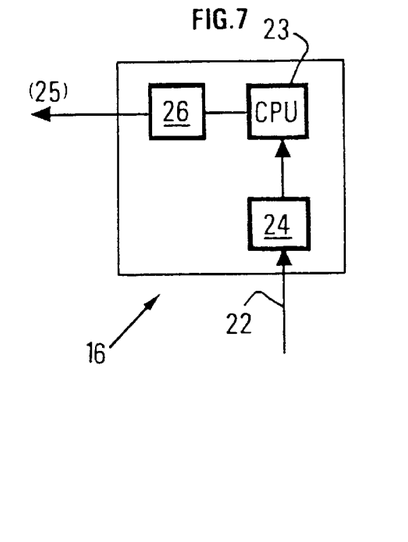
FIG. 7 shows the flowsheet of an external system for control and acquisition of the measuring signals, and FIG. 8 diagrammatically shows another embodiment suitable for measuring oil volume expelled from a sample by centrifugation in an gas-oil drainage mode.

Outer device 16 comprises (FIG. 7) a microprocessor 23 provided with a card 24 intended for acquisition of the various measuring signals produced by the various sondes 11 and transmitted by cables 15 and 22. Microprocessor 23 is connected to a control box 25 for controlling motor 18 (FIG. 6) by means of an interface card 26. The microprocessor computes the corresponding volume variations of the fluids from the measuring signals delivered by the various sondes 11, which are proportional to the height of conducting liquid in chambers 3, 4 of each vessel 2, the free volumes around samples 1 and spacers 6 being known.

II) Implementation

Figure 2:
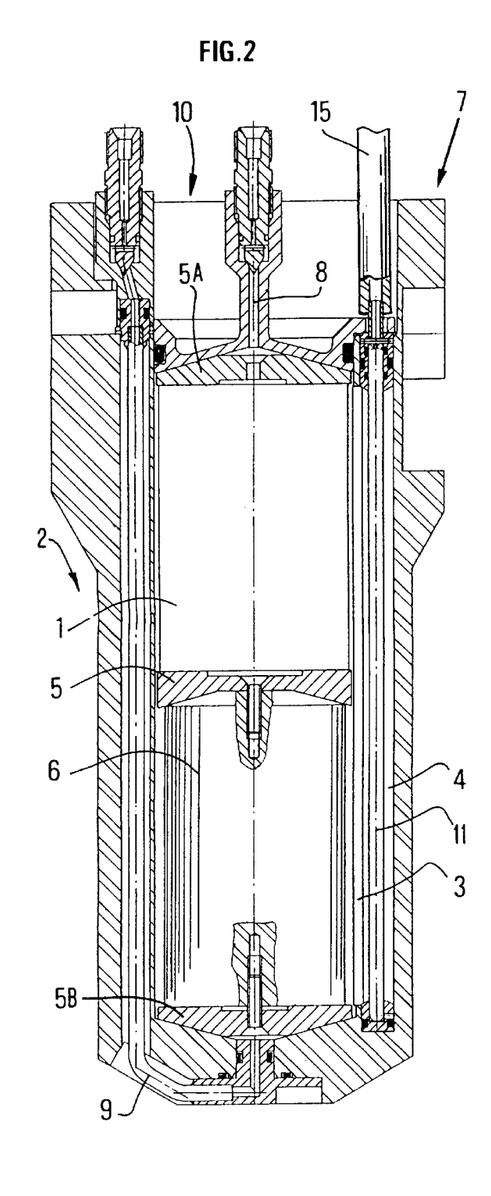
FIG. 2 shows a mode of installation, in a container or vessel, in its vertical position of rest when the centrifuge is stopped, of a sample to be centrifuged and of a spacer, suitable for drainage.
Figure 3:
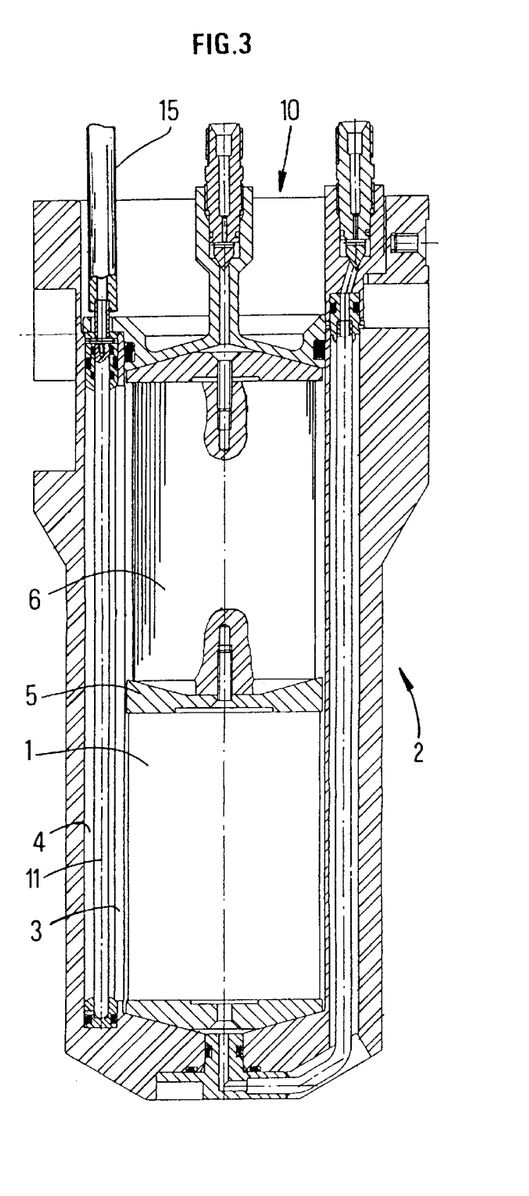
FIG. 3 shows a mode of installation, in a container or vessel placed in the same position, of a sample to be centrifuged and of a spacer, suitable for forced imbibition.

According to the respective position of sample 1 and of spacer 6 in each vessel 2, the device can be used for performing drainage phases and imbibition phases as well (embodiments of FIGS. 2, 3 respectively). For drainage, the sample is placed in the part of the vessel which is the closest to the shaft of motor 18 in operation (FIG. 2), in order to follow the production of conducting fluid (brine in the present case), whereas for imbibition, the sample is placed in the opposite part, i.e. the furthest part, in order to follow the production of oil (FIG. 3).

a) Water-oil drainage

A sample previously saturated with brine for example is placed in each vessel 2 containing oil, spacer 6 being placed (FIG. 2) so as to be at a further distance from the hub than the sample (at the bottom when stopped). A known amount of brine is injected at the base of the vessel through channel 9. Caps 10 are closed. The centrifuge is operated and its speed is increased in successive stages until a capillary equilibrium is obtained for each one of them. The signal produced by sonde 11 in response to the level variation of the water-oil interface is continuously recorded by microprocessor 23 of device 16 (FIG. 6). When the maximum speed stage is reached, the machine is stopped. The brine is removed from the vessel by injecting oil through channel 8 and the volume of brine produced is assessed by checking that it is equal to the volume calculated by device 16 from the measurement of sonde 11.

b) Water-oil forced imbibition

The sample is placed in vessel 2 filled with brine, the spacer being at the top (FIG. 3). A known amount of oil is injected through channel 8 until a certain level is reached. The rotating speed of the centrifuge is increased in successive stages until a capillary equilibrium is reached for each one. Similarly, the signals are continuously acquired and the amount of oil expelled from the sample is calculated. When the maximum speed stage is reached, the machine is stopped. The oil is removed by injecting brine through channel 9. The volume of oil produced is measured and compared with the volume continuously calculated by the microprocessor during centrifugation.

The previous operations can be repeated in order to measure the second drainage curves if need be.

The micro-computer 23 can also be programmed to perform directly computations of the petrophysical parameters deducible from the measurements performed during the drainage and imbibition cycles.

A preferred embodiment has been described, wherein the position of the interface between the two fluids in each vessel is measured by a sonde and the results are transmitted to a stationary outer acquisition device. Other interface monitors no can however be used without departing from the scope of the invention, such as notably a well-known system allowing reading of the interface levels through ports provided in the wall of the vessels.

Air-oil drainage:

The following implementation mode is used for measuring the oil volume expelled from an oil saturated sample resulting from a centrifugation.

Figure 8:
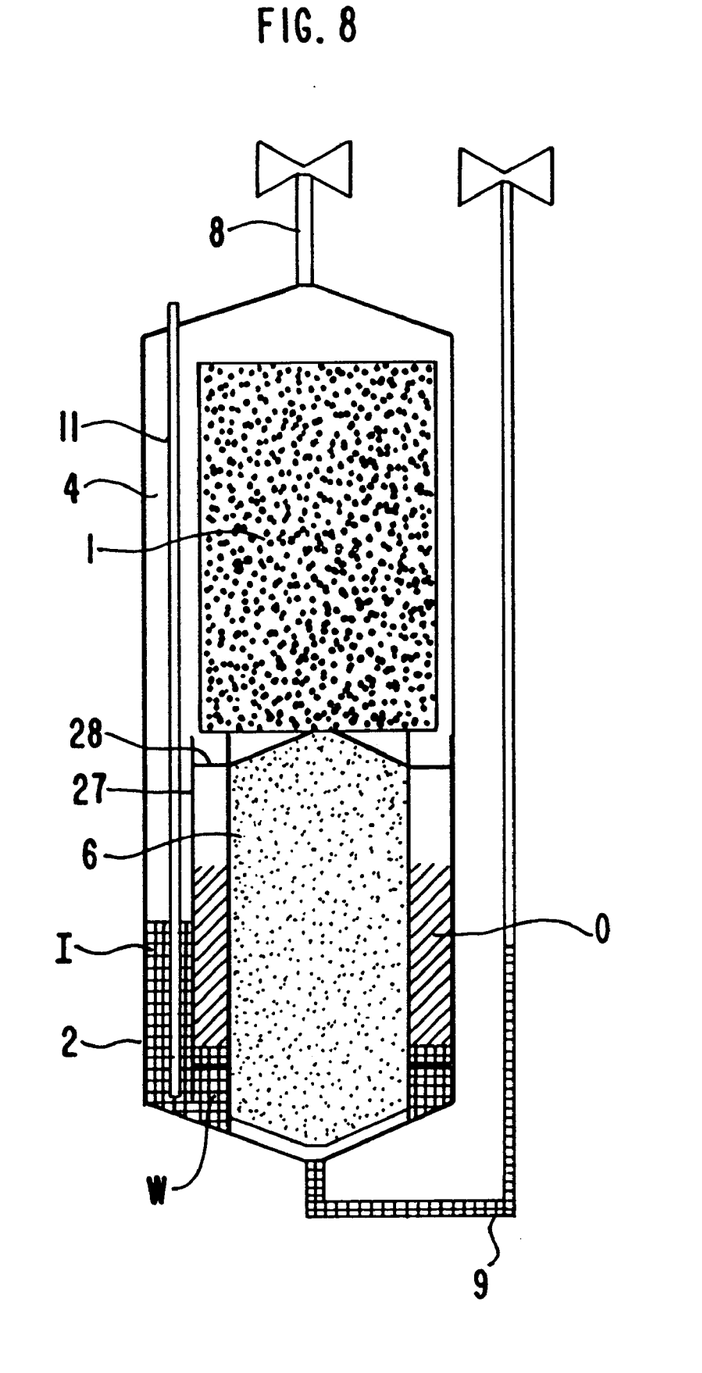

In this mode, the spacer 6 is positioned in a tube or container 27 made of an insulating material with a cross-section larger than the cross-section of the spacer, sufficient for collecting all the oil volume expelled from the sample 1. The spacer 6 is centered in the container 27 by centering ribs 28. An opening is provided at the bottom of the container 27 for communication with the lateral tubular chamber 6 containing the detecting sonde 11.

The oil saturated sample is placed in the vessel 2 filled with a gas such as air and a volume of water is initially introduced in the channel 9. The sample is then centrifuged and oil O expelled in the container 27 pushes water out of the base of the vessel 2 to the lateral chamber 4 where the level rises. The variation of the water level I in the chamber 4 is measured by the detecting sonde 11.

The cross-section of the spacer 6 is preferably selected in relation with the porosity of the sample 1 so that the total volume of oil expelled can take up in the annular space between the spacer and the container 27 and the displacement of interface I in the lateral chamber 4 is as large as possible so that the sensitivity of the capacitive sonde is optimum.

What is claimed is:

1. A process for measuring physical characteristics of a porous solid sample by performing drainage and imbibition operations on the porous sample in a presence of a first electrically-conductive fluid and of a second fluid of lower density than the first fluid, using a centrifugation assembly including at least one vessel provided with a chamber, each vessel being fastened to an end of an arm secured to a hub, and a rotational drive which drives each arm in rotation to create centrifugal force exerted in a radial direction along each vessel, comprising:

providing drainage and imbibition operations by centrifuging each vessel at a centrifugation speed which increases by steps until a capillary equilibrium is reached for each step, with the porous sample being positioned in each chamber together with a spacer made of a non porous material, the spacer volume being so selected that, in operation, the interface between the two fluids does not come into contact with the sample, after injecting a known amount of one of the first electrically-conductive fluid and the second fluid of a lower density into each chamber on a side thereof occupied by the spacer, with respective positions of the sample and of the associated spacer in each chamber being inverted according to whether the drainage operation or the imbibition operation is performed.

2. A process for measuring physical characteristics of a porous solid sample by performing drainage operations, in a presence of a first electrically-conductive fluid and of a second fluid of lower density than the first electrically-conductive fluid using a centrifugation assembly including at least one vessel each provided with a chamber, each vessel being fastened to an arm secured to a hub, a rotational drive which drives each arm in rotation which creates centrifugal force exerted in a radial direction along each vessel, a sonde for detecting, in each vessel, an interface between the first electrically-conductive fluid and the second fluid of a lesser density and a system, responsive to each sonde, which determines a volume of fluid channel drained from the sample, comprising:

a) placing in each chamber filled with a volume of the second fluid of a lesser density a sample previously saturated with the first electrically-conductive fluid and a spacer made of a nonporous material with the spacer positioned so as to be at a different distance from the hub than the sample;

b) injecting a known amount of the first electrically-conductive fluid into each chamber on the side thereof occupied by the spacer;

c) centrifugating each vessel at a centrifugation speed which increases by steps until a capillary equilibrium is reached for each step;

d) acquiring, during centrifuging, signals from each sonde representative of level variations of an interface between the first electrically-conductive fluid and the second fluid of lower density; and e) determining with the system a volume of the first fluid drained from the sample.

3. A process as claimed in claim 2, further comprising:

removing the first electrically-conductive fluid from each vessel by injecting a volume of the second fluid of lower density;

measuring a volume of removed first electrically-conductive fluid; and comparing the measured volume of the first electrically-conductive fluid with the volume determined by the system.

4. A process as claimed in claim 2, comprising:
a) placing in each chamber filled with a volume of the first electrically-conductive fluid a sample and a spacer made of a nonporous material, with the spacer positioned so as to be at a nearer distance from the hub than the sample;
b) injecting a known amount of the second fluid of lower density into each chamber on the side thereof occupied by the spacer;
c) centrifugating each vessel at a centrifugation speed which increases by steps until a capillary equilibrium is reached for each step;
d) acquiring, while centrifuging each vessel, signals from each sonde representative of level variations of an interface between the first electrically-conductive fluid and the second fluid of lower density; and
e) determining with the system a volume of the first electrically-conductive fluid imbibed by the sample.

5. A process as claimed in claim 3, comprising:
a) placing in each chamber filled with a volume of the first electrically-conductive fluid a sample and a spacer made of a nonporous material, with the spacer positioned so as to be at a nearer distance from the hub than the sample;
b) injecting a known amount of the second fluid of lower density into each chamber on the side thereof occupied by the spacer;
c) centrifugating each vessel at a centrifugation speed which increases by steps until a capillary equilibrium is reached for each step;
d) acquiring, while centrifuging each vessel, signals from each sonde representative of level variations of an interface between the first electrically-conductive fluid and the second fluid of lower density; and
e) determining with the system a volume of the first electrically-conductive fluid imbibed by the sample.

6. A process as claimed in claim 4, further comprising:
removing the second fluid of lower density from each vessel by injecting a volume of the first electrically-conductive fluid;
measuring a volume of removed second fluid of lesser density; and
comparing the measured volume of the second fluid of lower density fluid with the volume of the first electrically-conductive fluid determined with the system.

7. A process as claimed in claim 5, further comprising:
removing the second fluid of lower density from each vessel by injecting a volume of the first electrically-conductive fluid;
measuring a volume of removed second fluid of lesser density; and
comparing the measured volume of the second fluid of lower density fluid with the volume of the first electrically-conductive fluid determined with the system.

8. A process for measuring physical characteristics of a porous solid sample in a presence of a non-electrically-conducting fluid and a non-electrically-conducting gas, by using a centrifugation assembly including at least one vessel provided with a chamber, each vessel being fastened to the end of an arm secured to a hub, a rotational drive which drives each arm in rotation which creates centrifugal force exerted in a radial direction along each vessel, a sonde which detects, in each vessel, an interface between the non-electrically-conducting fluid and the non-electrically-conducting gas and a system, responsive to each sonde, which determines a position of the interface in each vessel, comprising:
placing the sample saturated with the non-electrically-conductive fluid in the at least one vessel filled with the non-electrically-conductive gas;
placing a spacer made of a nonporous material in a container, made of an insulating material positioned in the at least one vessel with the spacer positioned at a farther distance from the hub than the sample, to collect the non-electrically-conductive fluid drained from the sample;
injecting a volume of the non-electrically-conductive fluid in each container;
centrifugating the at least one vessel at a centrifugation speed which increased by steps until a capillary equilibrium is reached for each step; and
measuring with the system a displacement of an interface between the non-electrically-conductive fluid and the non-electrically-conductive gas.

9. A device for measuring physical characteristics of a porous solid sample by performing drainage phases, in a presence of a first electrically-conductive fluid and of a second fluid of lower density than the first fluid comprising:
a centrifugation assembly including at least one vessel provided with a main chamber, each vessel being fastened to an end of an arm secured to a hub, a rotational drive which drives each arm in rotation to produce centrifugal force exerted in a radial direction along each vessel, a detector which detects a position, in a side chamber of each vessel, of an interface between the first electrically-conductive fluid and the second fluid of lower density, a spacer disposed in each main chamber made of a nonporous material with the volume of the spacer being selected so that, in operation, the interface between the first electrically-conductive fluid and the second fluid of a lower density does not come into contact with the sample, the detector in each vessel including a sonde with a metallic rod coated with a layer of a dielectric material, each sonde being placed in the side chamber having a conducting wall adjacent the main chamber and a system, outside the centrifuging assembly, connected with each sonde through a rotating electric connector which measures capacitance variation detected by each sonde in contact with the first electrically-conductive fluid and the second fluid of lower density in each vessel resulting from an immersion thereof in the first electrically-conductive fluid, and which determines a volume of fluid displaced.

10. A device as claimed in claim 9, further comprising:
a container in each vessel, made of an insulating material, which receives the spacer, having a cross-section larger than a cross-section of the spacer, the container being positioned for collecting fluid expelled from the sample, with the container communicating with the side chamber.

11. A device as claimed in claim 10, wherein:
each container has a volume so that a total volume of the second fluid of lower density expelled from the sample substantially fills up a free volume in the container around the spacer so that a range of displacement of the interface resulting from a variation of volume of the first electrically-conductive fluid and the second fluid of lower density in the first chamber is maximized.

12. A device as claimed in claim 9, wherein each vessel comprises:

two channels communicating during rotation on opposite ends of each main chamber with an outside of an end of the vessel closest to the hub; and caps which insulate an inside of each main chamber during centrifugation.

13. A device as claimed in claim 10, wherein:

two channels communicating during rotation on opposite ends of each main chamber with an outside of an end of the vessel closest to the hub; and caps which insulate an inside of each main chamber during centrifugation.

14. A device as claimed in claim 11, wherein:

two channels communicating during rotation on opposite ends of each main chamber with an outside of an end of the vessel closest to the hub; and caps which insulate an inside of each main chamber during centrifugation.

15. A device as claimed in claim 9, wherein the centrifugation assembly comprises:

at least one pair of arms and vessels placed in opposition at ends respectively of the at least one pair of arms; and a pair of samples associated with each pair of arms.

16. A device as claimed in claim 10, wherein the centrifugation assembly comprises:

at least one pair of arms and vessels placed in opposition at ends respectively of the at least one pair of arms; and a pair of samples associated with each pair of arms.

17. A device as claimed in claim 16, wherein the centrifugation assembly comprises:

at least one pair of arms and vessels placed in opposition at ends respectively of the at least one pair of arms; and a pair of samples associated with each pair of arms.

18. A process as claimed in claim 2 wherein:

the spacer is positioned so as to be at distance farther from the hub than the sample.

19. A process as claimed in claim 3 wherein:

the spacer is positioned so as to be at distance farther from the hub than the sample.

* * * * *